(12) United States Patent
Hettrick et al.

(10) Patent No.: US 7,233,822 B2
(45) Date of Patent: Jun. 19, 2007

(54) COMBINATION OF ELECTROGRAM AND INTRA-CARDIAC PRESSURE TO DISCRIMINATE BETWEEN FIBRILLATION AND TACHYCARDIA

(75) Inventors: Douglas A. Hettrick, Blaine, MN (US); David E. Euler, Maple Grove, MN (US); Mark L Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 10/881,541

(22) Filed: Jun. 29, 2004

(65) Prior Publication Data

US 2005/0288725 A1    Dec. 29, 2005

(51) Int. Cl.
*A61B 5/04* (2006.01)
(52) U.S. Cl. .................................. 600/515; 600/518
(58) Field of Classification Search ............... 607/23
See application file for complete search history.

(56) References Cited

U.S. PATENT DOCUMENTS

| | | | |
|---|---|---|---|
| 4,316,472 A | 2/1982 | Mirowski et al. | 128/419 D |
| 4,375,817 A | 3/1983 | Engle et al. | 128/419 D |
| 4,384,585 A | 5/1983 | Zipes | 128/419 D |
| 4,577,633 A | 3/1986 | Berkovits et al. | 128/419 PG |
| 4,587,970 A | 5/1986 | Holley et al. | 128/419 PG |
| 4,726,380 A | 2/1988 | Vollmann et al. | 128/419 PG |
| 4,727,877 A | 3/1988 | Kallok | 128/419 D |
| 4,830,006 A | 5/1989 | Haluska et al. | 128/419 D |
| 4,880,005 A | 11/1989 | Pless et al. | 128/419 PG |
| 4,949,719 A | 8/1990 | Pless et al. | 128/419 D |
| 5,105,810 A * | 4/1992 | Collins et al. | 607/9 |
| 5,117,824 A | 6/1992 | Keimel et al. | 128/419 D |
| 5,161,527 A * | 11/1992 | Nappholz et al. | 607/14 |
| 5,163,427 A | 11/1992 | Keimel | 128/419 D |
| 5,188,105 A | 2/1993 | Keimel | 128/419 D |

(Continued)

FOREIGN PATENT DOCUMENTS

EP    0317065    5/1989

(Continued)

OTHER PUBLICATIONS

Kaye, Gerry C. et al., "Tachycardia Recognition and diagnosis from Changes in Right Atrial Pressure Waveform—A Feasibility Study," *PACE*, vol. 14, p. 1384-1392 (Sep. 1991).

*Primary Examiner*—Carl Layno
(74) *Attorney, Agent, or Firm*—Michael C. Soldner; Girma Wolde-Michael

(57) ABSTRACT

A system and method for detecting and classifying cardiac arrhythmias based on cardiac pressure signals or the combination of cardiac electrical and cardiac pressure signals. A cardiac electrogram signal is sensed to derive a cardiac rate from which an arrhythmia detection is made when the cardiac rate meets arrhythmia detection criteria. An intracardiac pressure signal is sensed to derive an indicator of tachycardia based on an analysis of the pressure signal in either the time domain or frequency domain. The detected arrhythmia is classified as tachycardia or fibrillation based on the tachycardia indicator wherein the tachycardia indicator is compared to tachycardia detection criteria and the arrhythmia is classified as tachycardia if tachycardia detection criteria are met and the arrhythmia is classified as fibrillation if the tachycardia detection criteria are not met.

31 Claims, 11 Drawing Sheets

U.S. PATENT DOCUMENTS

| | | | |
|---|---|---|---|
| 5,193,550 A * | 3/1993 | Duffin | 600/510 |
| 5,205,283 A * | 4/1993 | Olson | 607/4 |
| 5,261,401 A | 11/1993 | Baker et al. | |
| 5,324,326 A | 6/1994 | Lubin | 607/122 |
| 5,411,524 A | 5/1995 | Rahul | 607/4 |
| 5,535,752 A | 7/1996 | Halperin et al. | 128/670 |
| 5,564,434 A | 10/1996 | Halperin et al. | 128/748 |
| 5,782,876 A * | 7/1998 | Flammang | 607/4 |
| 5,899,927 A * | 5/1999 | Ecker et al. | 607/23 |
| 6,091,988 A | 7/2000 | Warman et al. | 607/5 |
| 6,095,984 A * | 8/2000 | Amano et al. | 600/500 |
| 6,185,460 B1 * | 2/2001 | Thompson | 607/16 |
| 6,599,242 B1 | 7/2003 | Splett et al. | |
| 6,873,870 B2 | 3/2005 | Ferek-Petric | |
| 7,024,244 B2 * | 4/2006 | Muhlenberg et al. | 607/23 |
| 2004/0167580 A1 * | 8/2004 | Mann et al. | 607/17 |

FOREIGN PATENT DOCUMENTS

EP 1410756 4/2004

\* cited by examiner

COMBINATION OF ELECTROGRAM AND INTRA-CARDIAC PRESSURE TO DISCRIMINATE BETWEEN FIBRILLATION AND TACHYCARDIA

FIELD OF THE INVENTION

The present invention relates generally to implantable cardiac stimulation and monitoring devices and particularly to a device and method for detecting and classifying arrhythmias using intracardiac pressure information.

BACKGROUND OF THE INVENTION

In the past, atrial arrhythmias have been largely undertreated due to the perception that these arrhythmias are relatively benign. As more serious consequences of persistent atrial fibrillation have come to be understood, such as an associated risk of relatively more serious ventricular arrhythmias and stroke, there is a greater interest in providing implantable atrial or dual chamber cardioverter defibrillators for treating atrial arrhythmias.

Atrial fibrillation (AF) can be treatable with relatively high voltage defibrillation shocks, which are generally painful to the patient, or high frequency pulse bursts. Atrial flutter (AFL), also referred to herein as atrial tachycardia (AT) can be treated by anti-tachycardia pacing (ATP) therapies, pulse bursts or cardioversion shocks. Generally, it is preferred to initially treat AFL with a less aggressive therapy such as ATP, which is not painful to the patient and requires less battery energy than cardioversion shocks. Reliable discrimination between AFL and AF is important in selecting the appropriate atrial arrhythmia therapy and is also useful in monitoring a patient's arrhythmia disease status, managing medical therapy, and evaluating the effectiveness of arrhythmia therapies.

In AFL, the atria beat at an elevated rate that is highly regular, typically at 200 to 320 beats per minute. While beating at a pathologically high rate, the atrial contraction can be sufficiently coordinated to generate pressure within the atria. In AF, the atria depolarize at an elevated rate that can be regular or irregular. The atrial contraction is disorganized, however, and not efficient enough to generate pressure. AFL, characterized by a single depolarizing wavefront, is often treatable by anti-tachycardia pacing (ATP) therapies, whereas AF, characterized by multiple depolarizing wavefronts, is not treatable by ATP therapies.

Clinically, the efficacy of atrial ATP therapies is reportedly, on the order of less than 50%. This low efficacy rate may not reflect the effectiveness of atrial ATP therapies in successfully treating AFL, but instead reflect inappropriate AFL detections resulting in the delivery of atrial ATP therapies during a rhythm that is untreatable by ATP. If the rhythm is in fact AF, atrial ATP therapies will be ineffective. On the other hand, arrhythmias classified as AF that are in fact fast AFL may be unnecessarily treated with a more aggressive arrhythmia therapy such as a shock therapy, needlessly exposing the patient to shock pain and consuming battery energy. Improved specificity of atrial arrhythmia classification methods may therefore allow ATP therapy efficacy to be improved and conservative but appropriate use of defibrillation shock therapies.

Methods for specifically classifying atrial arrhythmias, for monitoring or therapy selection purposes, generally depend only on atrial rate information in current commercially available devices. Such information may include the atrial rate and the regularity of the atrial rate. A range of atrial rates may be specified for detecting AFL and a different, generally higher, range of atrial rates may be specified for detecting AF. However, because the atrial rate could be the same during AFL and AF, specified ranges for AFL and AF detection may overlap and therefore rate information alone is not always adequate for detecting and discriminating AFL and AF. When an atrial rate is detected in this overlap range, atrial cycle length regularity may be used for discriminating between AFL and AF. However, because the atrial cycle length can be regular during AF in some patients, atrial cycle length regularity may not always be a dependable distinguishing factor in discriminating AFL from AF either.

Therefore, what is needed is a method and device for discriminating between atrial arrhythmias when atrial rate information is ambiguous in discriminating AFL from AF.

BRIEF DESCRIPTION OF THE DRAWINGS

Aspects of the present invention will be readily appreciated as they become better understood by reference to the following detailed description when considered in connection with the accompanying drawings, wherein.

DETAILED DESCRIPTION OF THE PREFERRED EMBODIMENTS

The present invention provides a system and method for detecting and classifying cardiac arrhythmias based on cardiac electrical and pressure signals. The method includes sensing an EGM signal to derive a cardiac rate; detecting an arrhythmia when the cardiac rate meets arrhythmia detection criteria; sensing an intracardiac pressure signal to derive an indicator of tachycardia; classifying the detected arrhythmia based on the sensed pressure signal wherein the derived indicator of tachycardia is compared to tachycardia detection criteria and the arrhythmia is classified as tachycardia if tachycardia detection criteria are met and the arrhythmia is classified as fibrillation if the tachycardia detection criteria are not met.

In one embodiment, an atrial EGM signal and an atrial pressure signal are sensed for the detection and classification of atrial arrhythmias. An indicator of atrial tachycardia, referred to herein as atrial flutter or "AFL," is derived from the atrial pressure signal using time-domain or frequency-domain signal analysis. An indicator of AFL determined using time-domain signal analysis methods may be an integral, a peak magnitude, average peak magnitude, average magnitude or other feature of the high frequency signal content, which, if greater than a predetermined AFL detection threshold value, indicates the presence of AFL. In other embodiments, an AFL indicator may be based on a correlation of gated signal averages or other indices of atrial pressure amplitude variability.

In embodiments employing frequency-domain signal analysis methods, and AFL indicator may be determined as an unexpected peak at a non-harmonic frequency of the underlying ventricular rate or as a comparative index of the low and high frequency magnitudes of a Fourier transform of the atrial pressure signal, e.g., a peak magnitude ratio, an average magnitude ratio, summed magnitude ratio, or magnitude difference, which may be compared to a predetermined AFL detection threshold value.

The present invention is realized in an implantable system including a cardiac stimulation or monitoring device and associated leads equipped with electrodes for sensing the cardiac EGM signal and a pressure sensor for sensing intracardiac pressure. The device includes sensor interfaces and signal processing circuitry for determining cardiac rate related information from the EGM signal and pressure information from the pressure signal. A control unit executes arrhythmia detection methods for detecting an arrhythmia based on rate information and classifying the arrhythmia based on pressure information. The device may include a therapy delivery unit for applying therapeutic electrical stimulation to the heart. An arrhythmia detection and classification made using the methods included in the present invention may be used for selecting and initiating an arrhythmia therapy.

Figure 1:
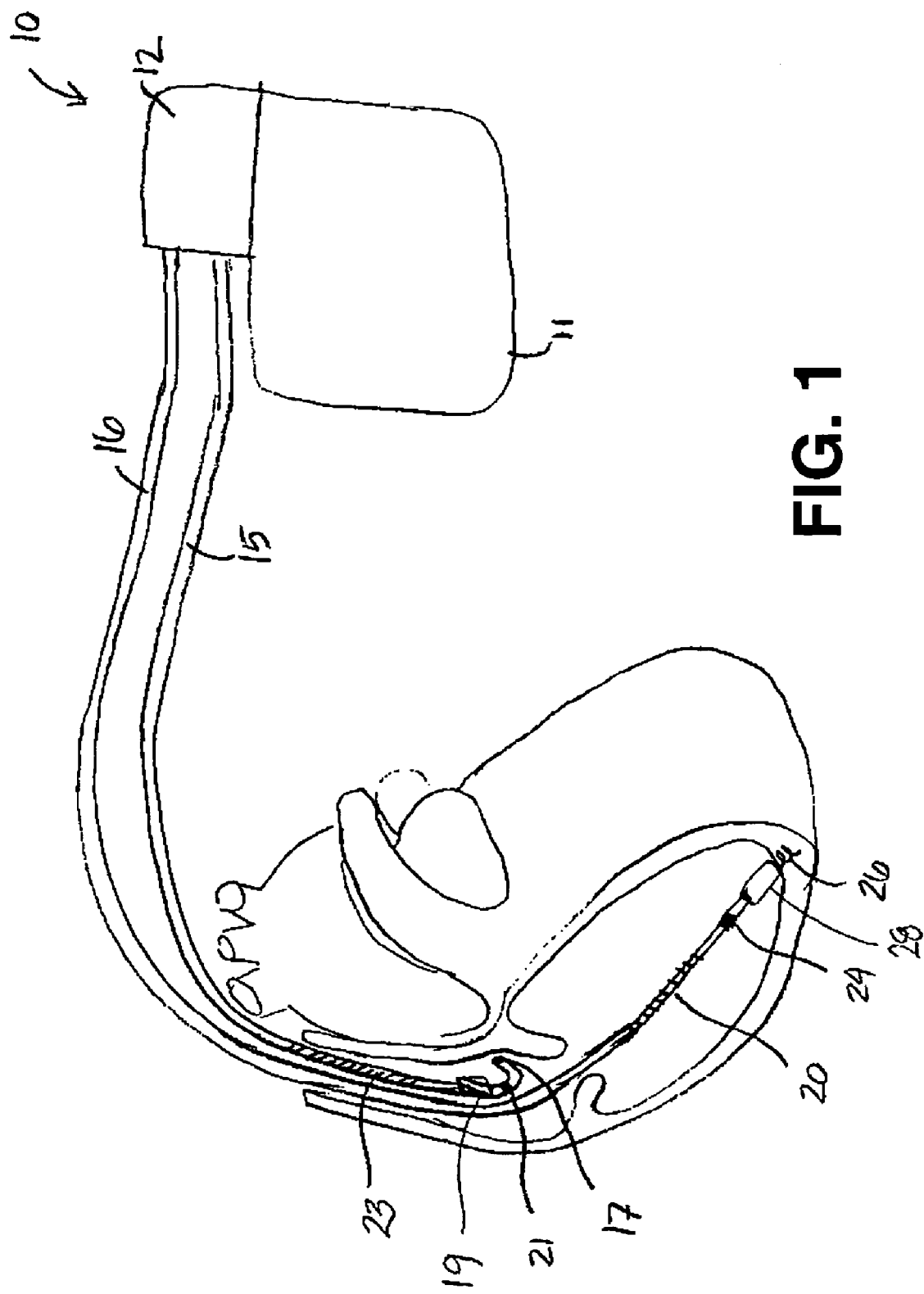
FIG. 1 is a schematic diagram of an exemplary implantable cardiac stimulation device in which the present invention may be practiced.

FIG. 1 is a schematic diagram of an exemplary cardiac stimulation device in which the present invention may be practiced. Device 10 is provided with dual-chamber pacemaking, cardioversion, and defibrillation capabilities. Dual chamber cardioverting and defibrillating devices sense both atrial and ventricular events for the detection of arrhythmias in both atrial and ventricular chambers. The present invention may be embodied in a single, dual or multichamber cardiac stimulation device. The present invention is expected to be particularly beneficial in discriminating AFL from AF. As such, a stimulation device in which the present invention is embodied includes at least atrial EGM and atrial pressure sensing capabilities and is preferably capable of delivering atrial arrhythmia therapies. Atrial arrhythmia therapies may include ATP therapies, high frequency pulse bursts, and/or higher voltage cardioversion and/or defibrillation pulses.

In dual or multichamber systems, the cardiac stimulation device may additionally be capable of sensing ventricular signals and delivering ventricular arrhythmia therapies and may provide bradycardia pacing or other types of cardiac stimulation therapies. While the present invention is expected to be particularly beneficial in discriminating AFL from AF, the invention may also be beneficial in discriminating ventricular arrhythmias, e.g., ventricular tachycardia from ventricular fibrillation. Furthermore, aspects of the present invention for detecting and classifying arrhythmias may be implemented in a cardiac monitoring device without having arrhythmia therapy delivery capabilities. However, to illustrate the benefits of the present invention, the preferred embodiments described herein relate to a dual chamber implantable cardioversion defibrillation device.

Device 10 of FIG. 1 is shown coupled to a patient's heart by way of a right atrial (RA) lead 15 and a right ventricular (RV) lead 16. A connector block 12 receives the proximal end of a right ventricular lead 16 and right atrial lead, used for positioning electrodes for sensing and stimulation. Right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by a standard connector assembly at the proximal end of lead 16 for providing electrical connection to the device 10.

The right atrial lead 15 is positioned such that its distal end is in the right atrium. Lead 15 is equipped with a ring electrode 21 and a tip electrode 17 for sensing and pacing in the right atrium. Lead 15 is further equipped with a superior vena cava (SVC) coil electrode 23 for delivering high-energy shock therapy. The ring electrode 21, the tip electrode 17 and the SVC coil electrode 23 are each connected to an insulated conductor with the body of the right atrial lead 15. Each insulated conductor is coupled at its proximal end to a connector carried by a connector assembly.

In accordance with the present invention, right atrial lead 15 is further equipped with a pressure sensor 19 for sensing right atrial pressure. Pressure sensor 19 may be embodied as generally disclosed in commonly-assigned U.S. Pat. Nos. 5,535,752 and 5,564,434, incorporated by reference herein in their entireties. Alternatively, pressure sensor 19 may be embodied as generally described in U.S. Pat. No. 5,324,326 issued to Lubin, incorporated herein by reference in its entirety, or any other pressure sensing modules adapted for sensing intra-cardiac pressure. While the embodiment shown in FIG. 1 includes an intracardiac pressure sensor positioned on a right atrial lead for sensing right atrial pressure, the present invention may employ other types of leads equipped with a pressure sensor for use in sensing a pressure signal in other heart chambers.

The electrodes 17 and 21 or 24 and 26 may be used as bipolar pairs, commonly referred to as a "tipto-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 20 or 23 for defibrillation of the atria or ventricles. It is recognized that alternate lead systems may be substituted for the lead system illustrated in FIG. 1.

While a particular dual-chamber ICD and lead system is illustrated in FIG. 1, methodologies included in the present invention may be adapted for use with other dual chamber, or single or multichamber ICD systems involving pace/sense and cardioversion/defibrillation electrodes which may be placed intracardially, epicardially and/or subcutaneously.

Figure 2:
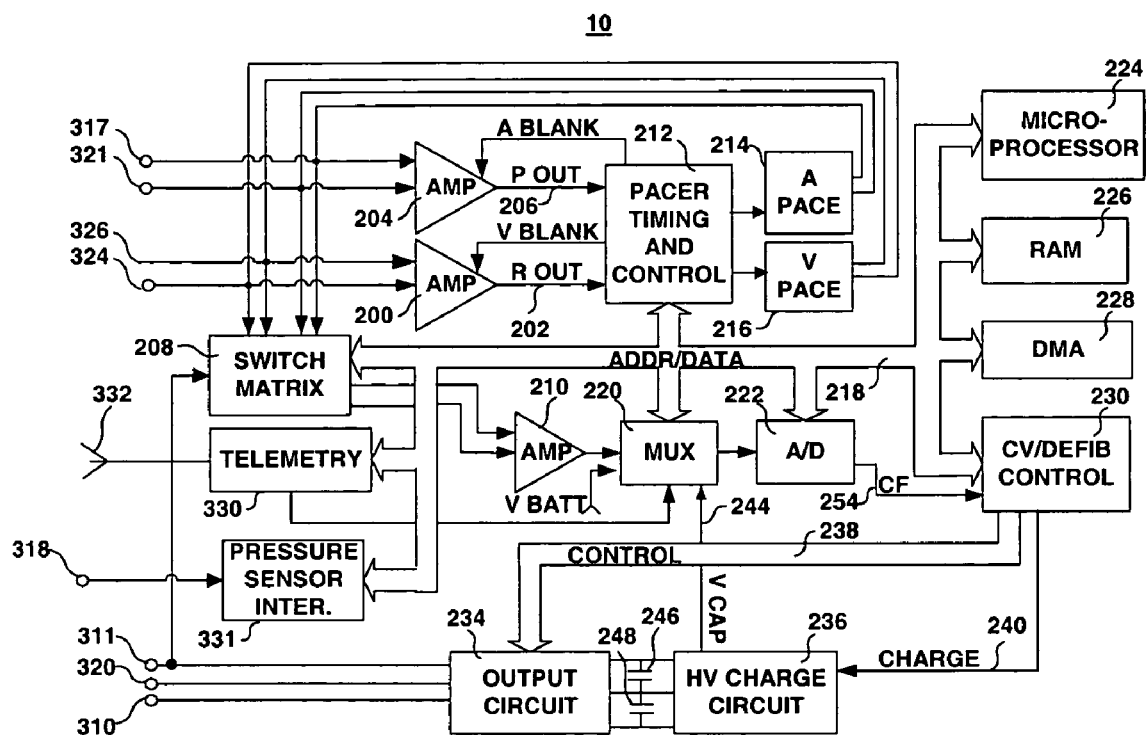
FIG. 2 is a functional block diagram of the cardiac stimulation device shown in FIG. 1.

FIG. 2 is a functional block diagram of the cardiac stimulation device shown in FIG. 1. This diagram should be taken as exemplary of the type of device with which the invention may be embodied and not as limiting, as it is believed that the invention may usefully be practiced in a wide variety of device implementations. For example, the disclosed embodiment shown in FIG. 2 is a microprocessor-controlled device, but the methods of the present invention may also be practiced with devices employing dedicated integrated circuitry for controlling some device functions.

With regard to the electrode system illustrated in FIG. 1, the ICD 10 is provided with a number of connection terminals for achieving electrical connection to the cardiac leads 15 and 16 and their respective electrodes. The connection terminal 311 provides electrical connection to the housing 11 for use as the indifferent electrode during unipolar stimulation or sensing. The connection terminals 310 and 320 provide electrical connection to coil electrodes 20 and 23. Each of these connection terminals 311, 310, and 320, are coupled to the high voltage output circuit 234 to facilitate the delivery of high energy shocking pulses to the heart using one or both of the coil electrodes 20 and 23 and optionally the housing 11.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm based on EGM information employing any of the numerous signal processing methods known in the art. As will be described further below, microprocessor 224 may additionally employ signal analysis techniques for evaluating an atrial pressure signal for using in classifying the patient's heart rhythm.

Device 10 further includes a pressure sensor interface 331 for receiving and processing a pressure signal received at terminal 318 from pressure sensor 19. Pressure sensor interface 334 may include various filters, amplifiers, and/or other circuitry for conditioning a pressure signal, in this embodiment a right atrial pressure signal. A right atrial pressure signal (or other intracardiac pressure signal) may be converted to a digital signal by A/D converter 222 for further signal processing by microprocessor 224.

The telemetry circuit 330 receives downlink telemetry from and sends uplink telemetry to an external programmer, as is conventional in implantable cardiac stimulation devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern implantable cardioverter defibrillators. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various dual-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R—R intervals, P—P intervals, P–R intervals, and R–P intervals, which measures are stored in memory 226 and for use in diagnosing the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. Any of the various arrhythmia detection methodologies known to the art may be employed in conjunction with the present invention for detecting and classifying arrhythmias.

In response to the detection of atrial flutter or ventricular tachycardia, an ATP therapy may be delivered if desired by loading a regimen from microcontroller 224 into the pacer timing and control circuitry 212 according to the type of tachycardia detected. Alternatively, circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman. Any known ventricular cardioversion or defibrillation pulse control circuitry may be usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., may be used in a device employing the present invention.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. Examples of high-voltage cardioversion or defibrillation output circuitry are generally disclosed in U.S. Pat. No. 4,727,877 issued to Kallok, and U.S. Pat. No. 5,163,427 issued to Keimel, incorporated herein by reference in their entireties.

In modern implantable cardioverter defibrillators, the particular therapies are programmed into the device ahead of time by the physician, and a menu of therapies is typically provided. For example, on initial detection of tachycardia, an ATP therapy may be selected. On redetection of tachycardia, a more aggressive ATP therapy may be scheduled. If repeated attempts at ATP therapies fail, a higher-level cardioversion pulse therapy may be selected thereafter. As in the case of currently available ICDs, and as discussed in the above-cited references, the amplitude of the defibrillation shock may be incremented in response to failure of an initial shock or shocks to terminate fibrillation. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

Figure 3:
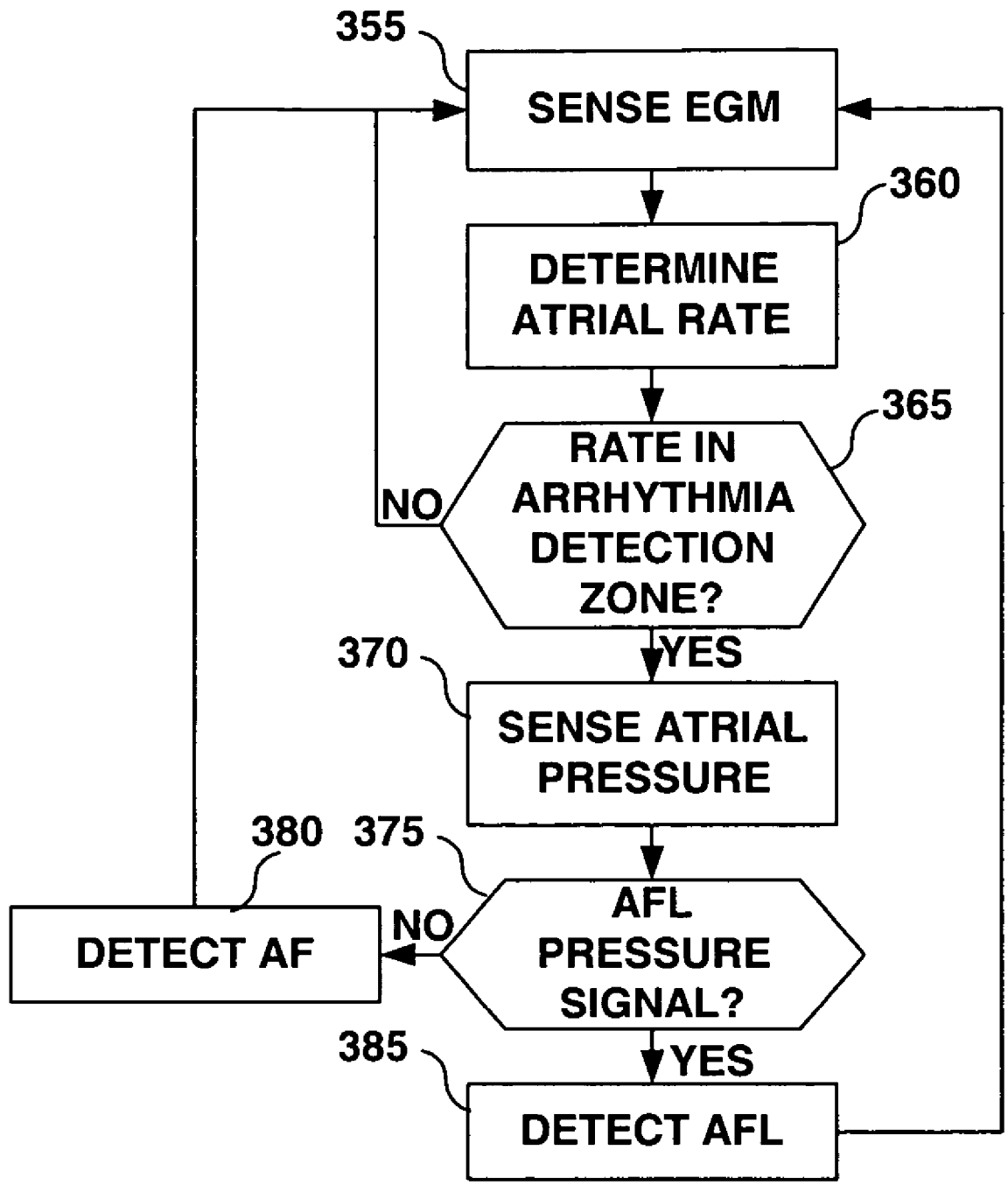
FIG. 3 is a flow diagram providing an overview of a method for detecting and classifying an atrial arrhythmia according to the present invention.

FIG. 3 is a flow chart providing an overview of a method for detecting and classifying an atrial arrhythmia according to the present invention. While method 350 shown in FIG. 3 is described with regard to the detection and classification of atrial arrhythmias based on a right atrial pressure sensor 19 as shown in FIG. 1, it is recognized that systems configured to measure a left atrial pressure may also utilize the methods described herein for detecting and classifying atrial arrhythmias. Furthermore, a pressure sensor may alternatively or additionally be positioned in the right ventricle or in operative relation to the left ventricle for sensing a ventricular pressure signal for use in detecting and classifying ventricular or atrial arrhythmias. Thus, the methods described herein with regard to atrial applications may be usefully practiced in ventricular applications of arrhythmia detection and classification as well.

At block 355, the atrial EGM signal is sensed using one or both of right atrial tip and ring electrodes 17 and 21. At block 360, the atrial rate is determined from the sensed EGM signal. The atrial rate may be determined based on P—P intervals according to methods known in the art. At decision block 365, microprocessor 224 determines if the atrial rate meets arrhythmia detection criteria. Typically, a predefined number of P—P intervals out of a given number of consecutive P—P intervals must be equal to or less than an arrhythmia detection interval. Arrhythmia detection intervals may be defined according to AFL and AF "zones" wherein the AFL detection intervals include one range of P—P intervals and AF detection intervals include a different range of P—P intervals that are typically shorter than the AFL detection intervals. The AFL and AF detection zones may, however, overlap.

In one embodiment, atrial pressure sensing is enabled, block 370, if a high atrial rate is detected regardless of whether the rate falls within the AFL, AF or overlap zone. In other embodiments, atrial pressure sensing may be enabled, block 370, only if the atrial rate falls within the overlap zone to provide an additional parameter to discriminate between AFL and AF when rate information alone is ambiguous.

It is further recognized that atrial pressure sensing may be enabled prior to rate-related arrhythmia detection criteria being satisfied. For example, atrial pressure sensing may be enabled as soon as a predefined number of one or more fast P—P intervals are sensed rather than waiting for rate-related arrhythmia detection criteria to be satisfied.

At block 375, the atrial pressure signal is analyzed to determine if the frequency content of the pressure signal indicates the presence of AFL. Methods for evaluating the atrial pressure signal for indicators of AFL will be described in detail below. Such indicators relate to the atrial contribution to the measured pressure signal. If the atrial pressure signal indicates the presence of AFL, AFL is detected at block 385. If the atrial pressure signal does not indicate the presence of AFL, AF is detected at block 380. The arrhythmia detection and classification made at block 380 or 385 may be used to trigger an appropriate arrhythmia therapy or menu of therapies. For example, the detection of AFL may trigger ATP therapy delivery whereas an AF detection may trigger a defibrillation shock.

The AF or AFL episode detection and the duration of the episode may be logged in device memory, as is conventional in implantable cardioverter defibrillator devices, such that a history of detected arrhythmias is available to a physician. The improved accuracy of atrial arrhythmia classifications made based on pressure monitoring provides more specific and accurate data regarding the number and duration of AFL and AF episodes, improving the utility of the device reported diagnostics.

As such, it is desirable to update the atrial rhythm classification on a continuous or periodic basis during a sustained AFL/AF detection since the rhythm may transition between AF and AFL during a single episode. Such transitions are important to detect for both monitoring and data storage and for therapy selection purposes. Therefore, after initially classifying an atrial arrhythmia as AF or AFL at blocks 380 or 385, respectively, the method shown in FIG. 3 may return to block 355, and, as long as the rate remains in an arrhythmia detection zone as determined at block 365, pressure monitoring continues at block 370 to allow ongoing analysis of the pressure signal at block 375 for updating or reclassifying a sustained atrial arrhythmia episode. Depending on the method used for deriving an AFL indicator, such updating may be repeated on each ventricular cycle, a predetermined number of ventricular cycles, or a predetermined interval of time.

Figure 4A:
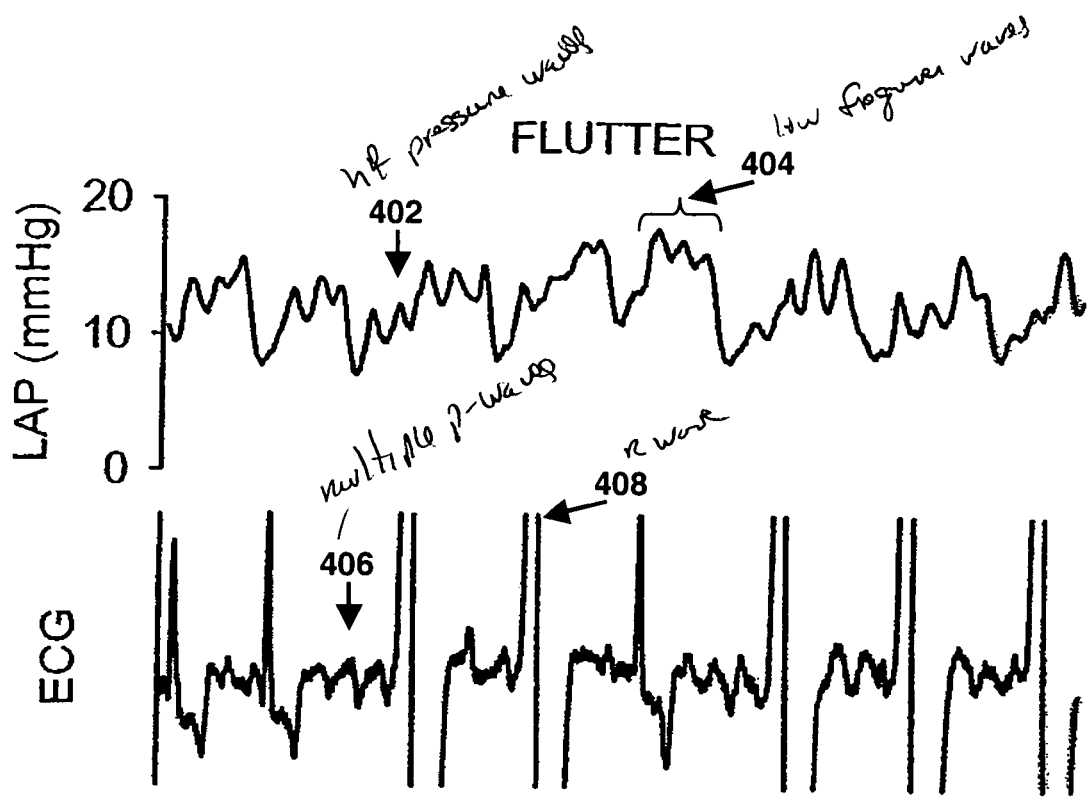
FIG. 4A is a sample recording of left atrial pressure (LAP) and ECG during induced AFL.
Figure 4B:
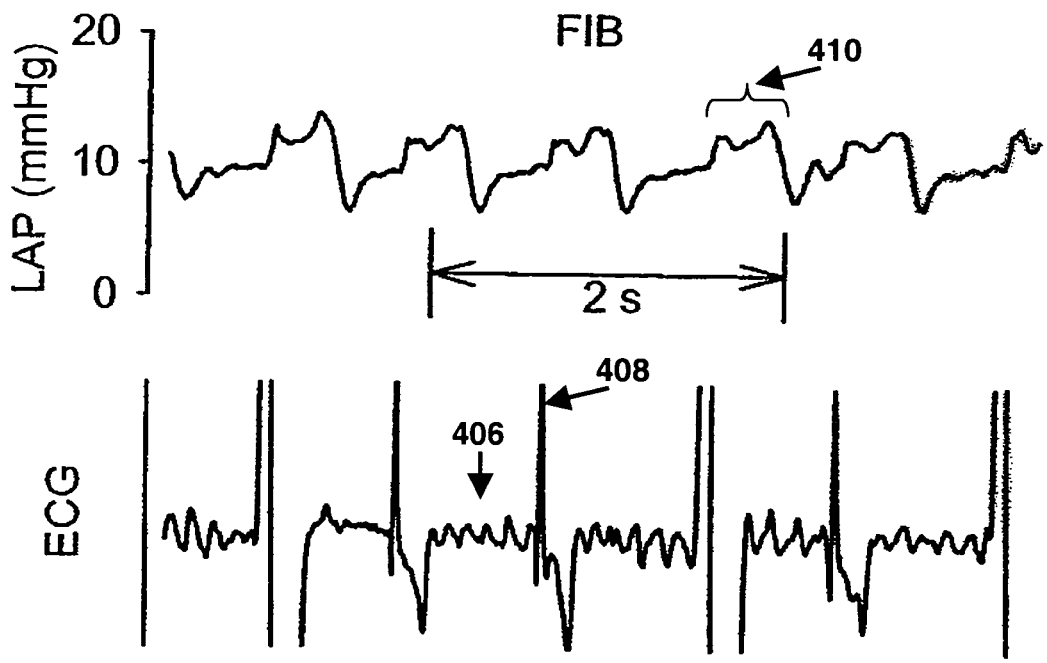
FIG. 4B is a sample recording of LAP and ECG during induced AF.

FIG. 4A is a sample recording of left atrial pressure (LAP) and ECG during an exemplary induced AFL episode, and FIG. 4B is a sample recording of LAP and ECG during an exemplary induced AF episode. The ECG recordings are similar in appearance in that multiple P-waves 406 can be observed between each R-wave 408. The LAP signal during AFL is observed to contain high frequency pressure waves 402 resulting from the rapid atrial rate that remains sufficiently coordinated to generate a small pressure pulse. The low frequency pressure waves 404 reflect the passive filling and emptying of the atria corresponding to the ventricular rate.

In FIG. 4B, the LAP signal obtained during AF does not exhibit the high-frequency pressure waves 402 observed during AFL. The passive filling and emptying of the atrium corresponding to the ventricular rate contributes to the dominant low frequency pressure waves 410.

Ventricular pressure monitoring is also contemplated for use in deriving an indicator of AFL. A ventricular pressure signal is similar to the atrial pressure signal during the ventricular filling phase of the cardiac cycle. Therefore, a pressure sensor positioned in the right or left ventricle may be used to obtain a ventricular pressure signal. The signal obtained during the ventricular filling phase may undergo signal processing for deriving an indicator of AFL that relates to the atrial contribution to the ventricular pressure signal during the filling phase.

Figure 5A:
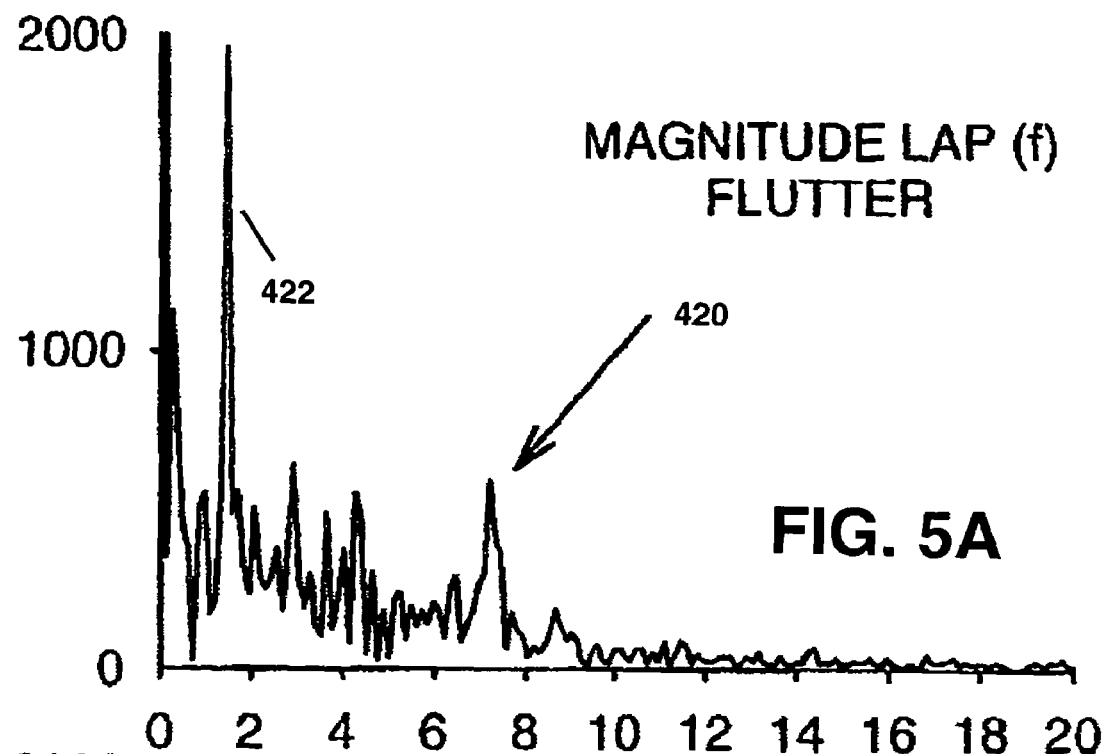
FIGS. 5A and 5B are graphs of the Fourier transform of the LAP signals shown in FIGS. 4A and 4B, respectively.
Figure 5B:
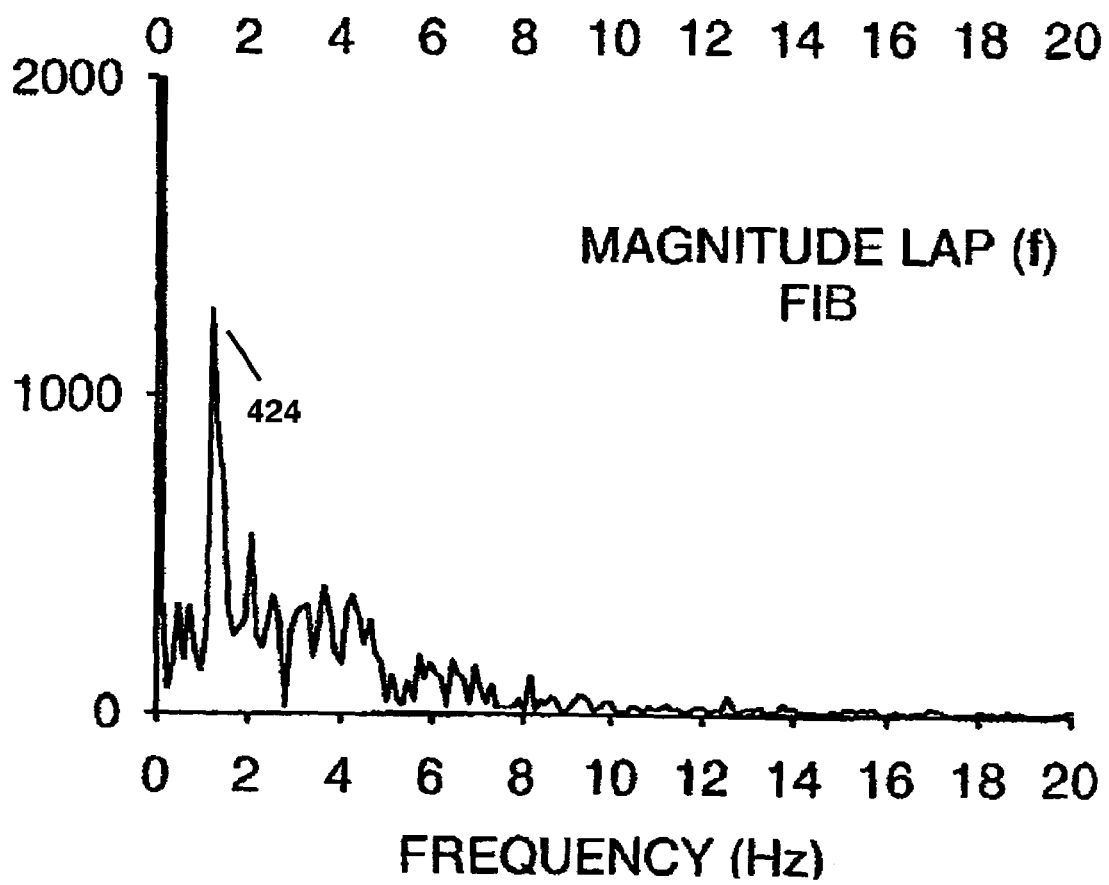

FIGS. 5A and 5B are graphs of the Fourier transform of the LAP signals shown in FIGS. 4A and 4B. In FIG. 5A, the Fourier transform of the LAP signal during AFL shows a high amplitude peak 420 at a frequency of approximately 7 Hz corresponding to the high frequency pressure waves produced by atrial contractions. A dominant peak 422 at approximately 1.5 Hz corresponds to the low frequency pressure waves associated with passive atrial filling and emptying due to ventricular function.

As shown in FIG. 5B, the energy content at higher frequencies is substantially less during AF than during AFL indicating little or no atrial contribution to the LAP signal due to the high, disorganized atrial rate. A dominant low-frequency peak 424 associated with ventricular function is observed.

The difference in frequency content of the atrial pressure signal during AFL and AF, readily observed in FIGS. 5A and 5B, may advantageously be used in discriminating between these rhythms in an arrhythmia detection algorithm. It is conceivable that numerous signal processing methods may be applied to an atrial pressure signal to ascertain whether the high frequency content of the pressure signal is indicative of the presence of AFL. Such methods may be frequency-domain or time-domain based, methods. Signal processing and analysis may be implemented in dedicated integrated circuitry included in sensor interface 331 from which an output signal indicating the status of an AFL indicator is generated for receipt by microprocessor 224. Alternatively, signal processing and analysis may be implemented at least in part in firmware resident in microprocessor 224.

Figure 6:
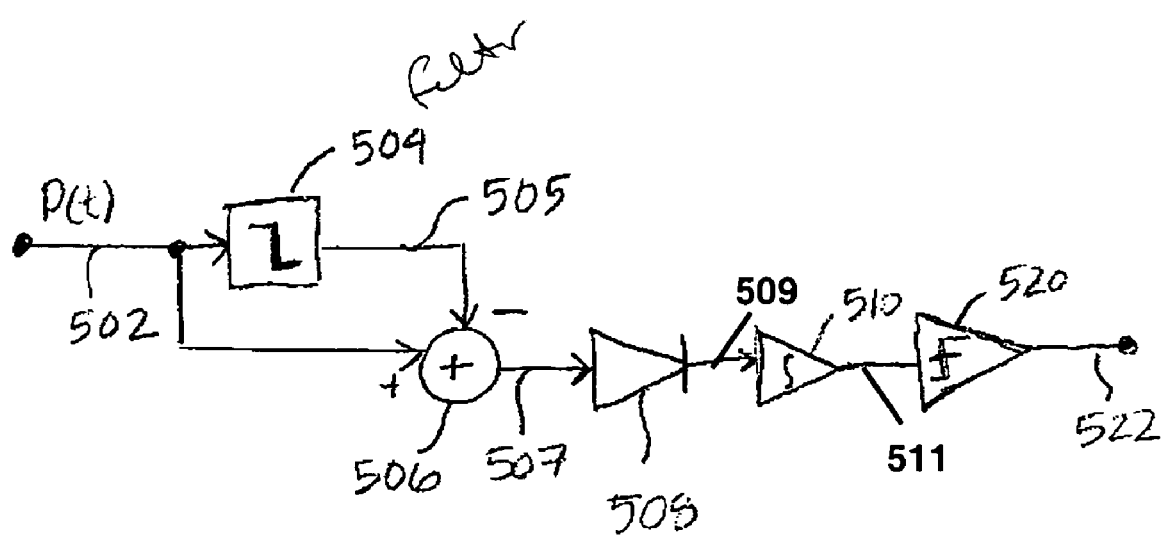
FIG. 6 is a functional block diagram depicting one method for processing an atrial pressure signal for determining if a high-frequency contribution due to AFL is present.

FIG. 6 is a functional block diagram depicting one method for processing an atrial pressure signal for determining if a high-frequency contribution due to AFL is present. An atrial pressure signal 502 is received as input to a filter 504 and as the positive input to a summing block 506. P(t) is preferably sampled at a rate of about 20 Hz or more in order to measure the high frequency content during AFL. Filter 504 is a low pass filter, for example a 4 Hz low pass filter designed to pass low frequency pressure components that would be associated with sinus rhythm and the ventricular contribution to the atrial pressure signal during high atrial rates and remove the high frequency pressure signals that would be associated with AFL.

The output 505 of filter 504 is provided as the negative input to summing block 506. The output 507 of summing block 506, which is the difference between the raw pressure signal 502 and the filtered signal 504, will contain only the high frequency pressure signal components. This difference output signal 507 is provided as input to rectifier 508, and the rectified signal 509 is integrated by integrator 510. The integrated signal 511 is compared to a predetermined threshold by threshold detector 520. If the integral of the rectified high-frequency signal exceeds a predetermined threshold, AFL is indicated based on a relatively high content of high-frequency signals. If the integral of the high-frequency signal does not exceed a predetermined threshold, AF is indicated. The indication of AFL or AF may be made according to a signal output 522 of threshold detector 520. Thus, in this embodiment, an AFL indicator is determined as the integral of the rectified, high frequency component of the pressure signal.

The integral may be determined over one or more cardiac cycles. Alternatively, an integral of the rectified high frequency component of the pressure signal may be determined over each cardiac cycle for a number of cardiac cycles. The integral for each cardiac cycle may be compared to an AFL detection threshold and AFL may be detected when a predetermined number of cardiac cycle integrals exceed the AFL detection threshold. A threshold value may be set to a nominal value by a physician based on clinical experience, or selected based on measurements of atrial pressure in an individual patient during normal sinus rhythm and/or during episodes of AFL and AF.

Figure 7:
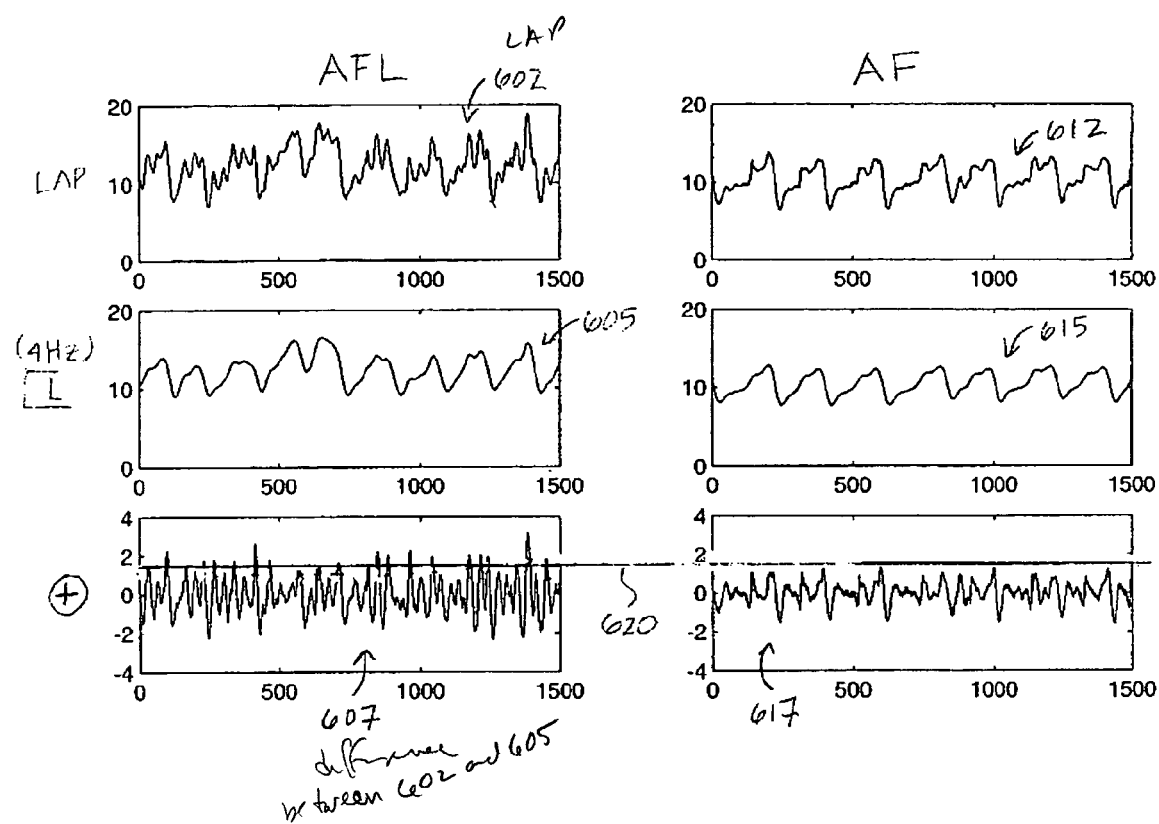
FIG. 7 depicts a set of sample atrial pressure recordings, including the raw atrial pressure signal and the signal obtained after the filtering and summing included in the processing method described in conjunction with FIG. 6.

FIG. 7 depicts a set of sample atrial pressure recordings, including the raw atrial pressure signal and the signal obtained after the filtering and summing blocks included in the processing method described in conjunction with FIG. 6. The LAP signal 602 was recorded during AFL (top left panel) and, in the signal processing method of FIG. 5, the raw LAP signal would be provided as the input pressure signal P(t) 502. Signal 605 is the filtered signal during AFL and would correspond to output 505 of filter 504 of FIG. 6. In this example, 4 Hz filtering has been performed. Signal 607 is the signal resulting from determining the difference between pressure signal 602 and filtered signal 605. Signal 607 corresponds to the output 507 of summing block 506 in FIG. 6 where pressure signal 602 is received as positive input to summing block 506 and filtered signal 605 is received as negative input. The resulting signal 607 represents the high frequency content of pressure signal 602 during AFL.

The three plots shown on the right in FIG. 7 correspond to signals acquired during AF. The top right panel is the LAP signal 612 received during AF corresponding to input signal 502 of FIG. 6. The middle right panel is the filtered signal 615 that would correspond to output 505 of filter 504 in FIG. 6. The bottom right panel is the high frequency content of pressure signal 612 obtained after determining the difference between pressure signal 612 and filtered signal 615. The high frequency signal 617 corresponds to the output 507 obtained after summing block 506 of FIG. 6.

By comparing high frequency signal 607 during AFL and high frequency signal 617 during AF, it is readily seen that the high frequency signal is of greater energy during AFL than during AF. Numerous methods may be proposed for discriminating between this high frequency energy difference. As proposed above in conjunction with FIG. 6, the high frequency signal may be rectified and integrated and the resulting value compared to a predetermined threshold value, which if exceeded indicates the presence of AFL.

Alternatively, a maximum or averaged peak amplitude of the high frequency signal may be compared to a predetermined threshold value 620 as shown in FIG. 7, which, if exceeded, indicates the presence of AFL. In yet another embodiment, the mean amplitude of the rectified or non-rectified high frequency signal may be compared to a predetermined threshold value. Thus, in time-domain based methods, an AFL indicator derived from an atrial pressure signal may be an integral, a peak magnitude, average peak magnitude, average magnitude or other feature of the high frequency signal content, which, if greater than a predetermined AFL detection threshold value, indicates the presence of AFL.

Figure 8:
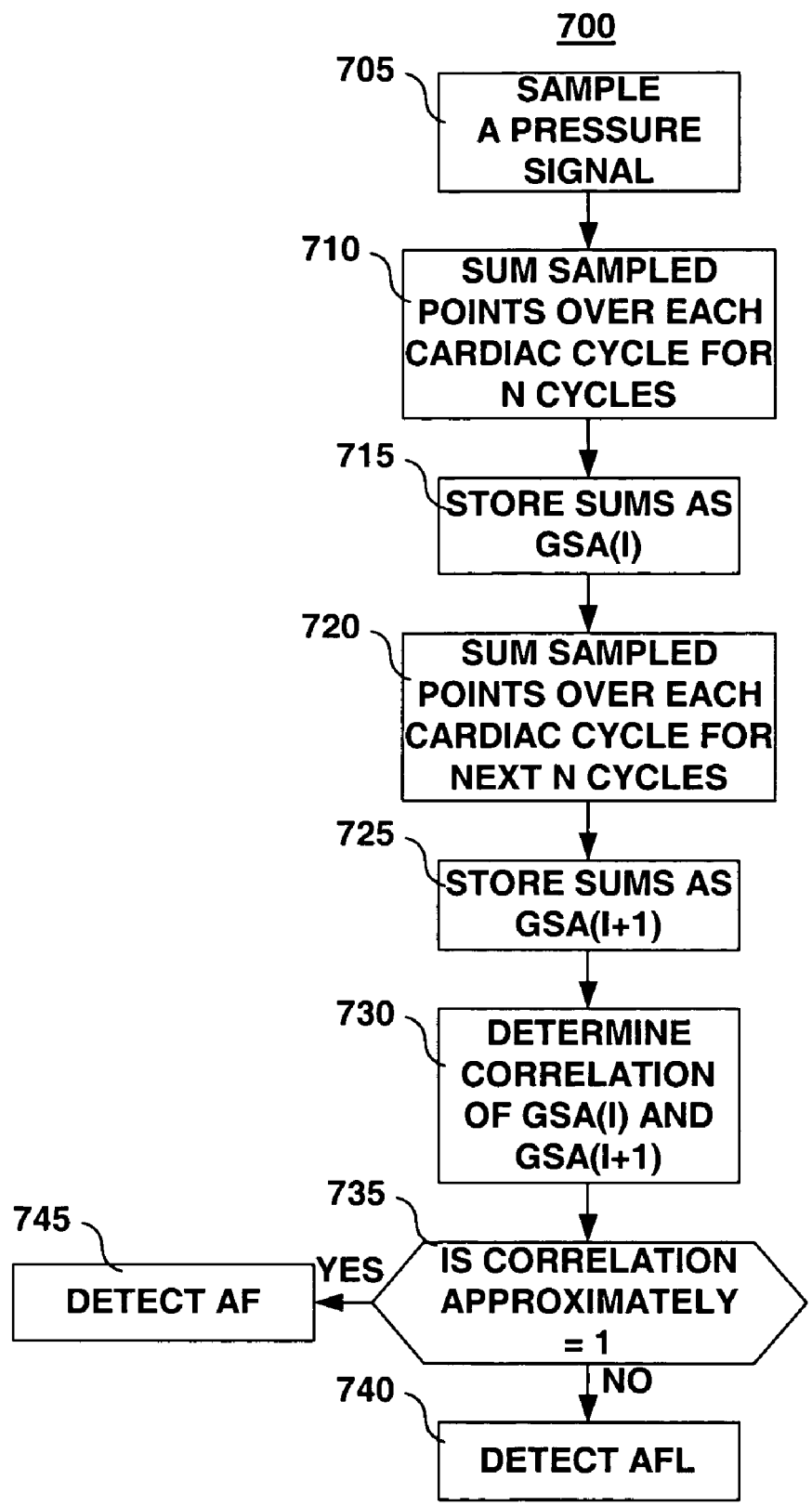
FIG. 8 is a flow chart of an alternative method for determining if an atrial pressure signal is indicative of AFL or AF in a time-domain analysis, according to the present invention.

FIG. 8 is a flow chart of an alternative method for determining if an atrial pressure signal is indicative of AFL or AF, according to the present invention. The method 700 is also performed in the time domain and involves determining a gated signal average of the atrial pressure signal over a number of cardiac cycles and determining the correlation of the gated signal average to another gated signal average determined from a preceding number of cardiac cycles. During AF, the variation between the atrial pressure signals from one cardiac cycle to the next is expected to be small when ventricular function is normal because the atria are not substantially contributing to the atrial pressure changes. During AFL, greater variation between atrial pressure signals from one cardiac cycle to the next is expected due to the contribution of pressure generation by the rapid atrial contractions. As such, the variation in the pressure signal amplitude may be examined to discriminate AFL from AF.

In one method 700, an atrial pressure signal is sampled at block 705 at a sampling rate sufficient to capture the high frequency components that may be present during AFL. At block 710, a summation of all data points sampled during a single cardiac cycle is determined. Cardiac cycle boundaries are preferably determined by sensed R-waves. Alternatively, cardiac cycle boundaries could be determined from the low frequency component of the pressure signal directly (as in FIG. 5). A summation of sample points may be computed for a predetermined number, N, of cardiac cycles, which may be one or more cardiac cycles. The summation(s) determined for each cardiac cycle are stored as the gated signal average(s) (GSA) for a first epoch, l, of N cardiac cycles at block 715.

At blocks 720 and 725, a summation of the sampled pressure signal points is determined for each cardiac cycle during the next epoch, l+1, and stored as the gated signal averages at block 725. At block 730, the correlation between the gated signal averages stored during the first epoch, GSA(l), and the gated signal averages stored during the subsequent epoch, GSA(l+1), is determined. If the correlation is approximately 1, i.e. the GSAs during the first epoch are approximately equal to the GSAs during the second epoch, a provisional atrial arrhythmia detection based on atrial rate is classified as AF at block 745. If the correlation is substantially different than 1, for example less than a predetermined value less than 1, a provisionally detected arrhythmia is classified as AFL at block 740. In other embodiments, a standard deviation of the sample point amplitudes or other statistical parameter for measuring pressure wave amplitude variation may be determined as an AFL indicator and compared to a threshold value.

Figure 9:
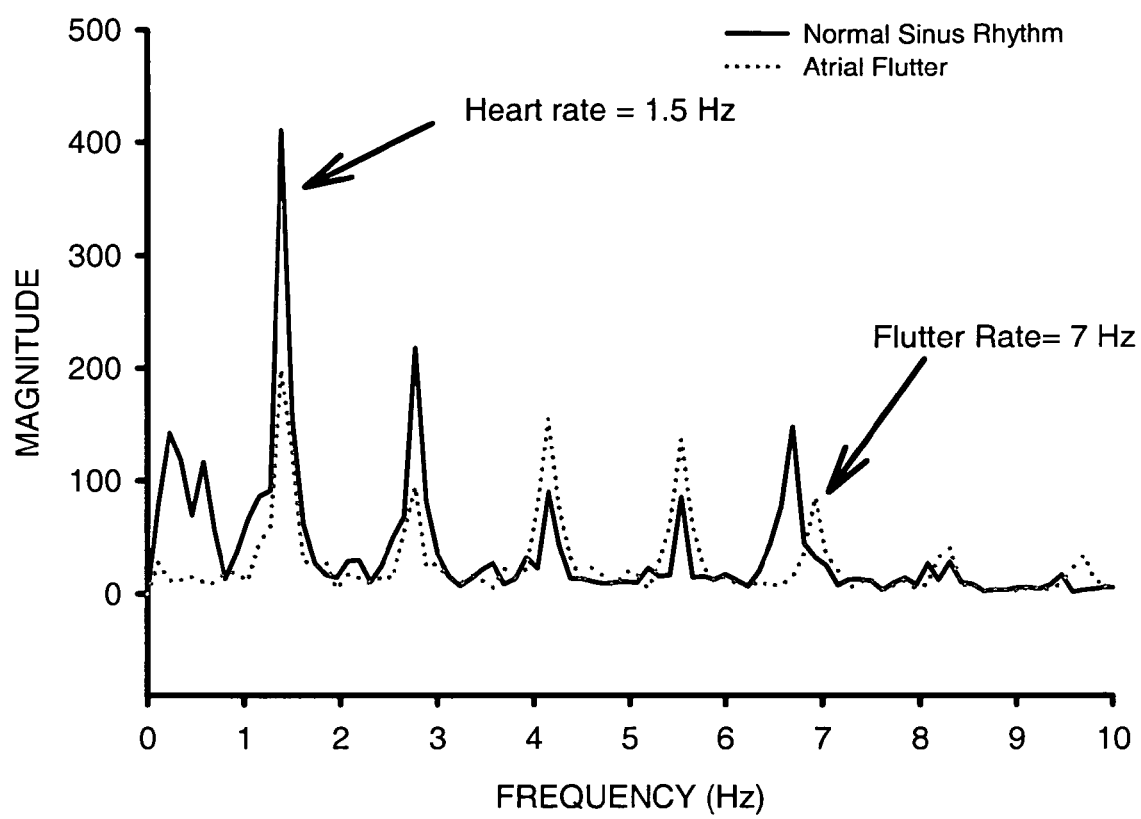
FIG. 9 is an example plot of the magnitude of the fundamental frequency and corresponding harmonics during normal sinus rhythm (NSR) and AFL.

Frequency-domain analyses may alternatively be used for determining if the high-frequency content of an atrial pressure signal is indicative of AFL. FIG. 9 is an example plot of the magnitude of the fundamental frequency and corresponding harmonics during normal sinus rhythm (NSR) and AFL. If the ventricular rate corresponds to a frequency of approximately 1.5 Hz (i.e., approximately 90 bpm), a dominant peak during NSR occurs at this fundamental frequency of approximately 1.5 Hz and smaller peaks occur at the corresponding harmonics.

When AFL is present, an unexpected peak may occur at a frequency corresponding to the atrial rate. In the example shown in FIG. 9, an unexpected peak occurs at approximately 7 Hz that does not correspond to a harmonic of the fundamental frequency of 1.5 Hz. This unexpected peak is evidence of a high frequency atrial pressure component due AFL. The 7 Hz frequency component corresponds to an atrial rate of approximately 420 bpm. Thus one method for evaluating an atrial pressure signal for deriving an indicator of AFL involves sampling an atrial pressure signal; performing a Fourier transform of the sampled data; determining the fundamental frequency associated with the low-frequency dominant peak; determining if any higher frequency peaks occur at non-harmonic frequencies; classifying an atrial arrhythmia as AFL if a non-harmonic peak is present and otherwise classifying an atrial arrhythmia as AF.

Figure 10A:
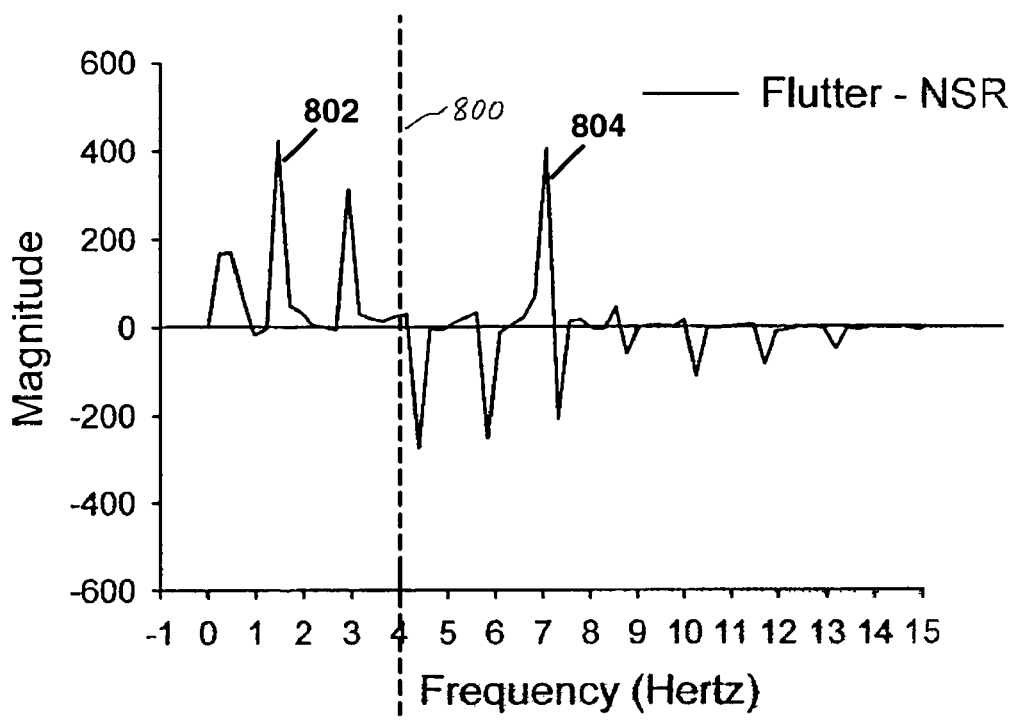
FIG. 10A is a plot of the difference in the magnitude of the Fourier transform of an atrial pressure signal during AFL and normal ventricular rhythm depicting an alternative method for deriving an indicator of AFL from an atrial pressure signal in a frequency domain analysis.

FIG. 10A is a plot of the difference in the magnitude of the Fourier transform of an atrial pressure signal during AFL and normal ventricular rhythm depicting an alternative method for deriving an indicator of AFL from an atrial pressure signal in a frequency domain analysis. A threshold frequency 800 may be set to allow a comparative analysis of the energy content below and above the threshold frequency 800. In one embodiment, a ratio of the dominant peak magnitude 804 occurring above the threshold frequency 800 to the dominant peak magnitude 802 occurring below the threshold frequency 800 may be determined and compared to a predetermined AFL detection threshold. If the ratio of the dominant peak magnitude 804 above the threshold frequency 800 to the dominant peak magnitude 802 below the threshold frequency 800 is greater than a predetermined AFL detection threshold, a provisionally-detected atrial arrhythmia based on atrial rate is classified as AFL based on atrial pressure. If the ratio is less than an AFL detection threshold, a provisionally-detected atrial arrhythmia is classified as AF.

Alternatively, an average energy (magnitude) above threshold frequency 800 and an average energy below the threshold frequency 800 may be determined. A ratio of the "high" frequency average energy to the "low" frequency average energy may be compared to an AFL detection threshold. In yet another embodiment, a summed magnitude ratio may be determined as the ratio of the summation of the magnitudes of all peaks above the threshold frequency 800 to the summation of the peak magnitudes below the threshold frequency 800. This summed magnitude ratio may be compared to an AFL detection threshold. If an average energy ratio or a summed magnitude ratio is greater than a predefined AFL detection threshold, a provisionally detected atrial arrhythmia is classified as AFL and otherwise classified as AF.

In still another embodiment, the difference between the dominant peak magnitude 802 below the threshold frequency 800 and the dominant peak magnitude 804 above the threshold frequency 800 may be determined. If this difference is less than an AFL detection threshold, AFL may be detected whereas if the difference is greater than an AFL detection threshold, AF may be detected.

Thus, in a frequency-domain analysis, an AFL indicator may be determined as an unexpected peak at a non-harmonic frequency of the underlying ventricular rate or as a comparative index of the low and high frequency magnitudes, e.g., a peak magnitude ratio, an average magnitude ratio, summed magnitude ratio, or magnitude difference, which may be compared to a predetermined AFL detection threshold value.

Figure 10B:
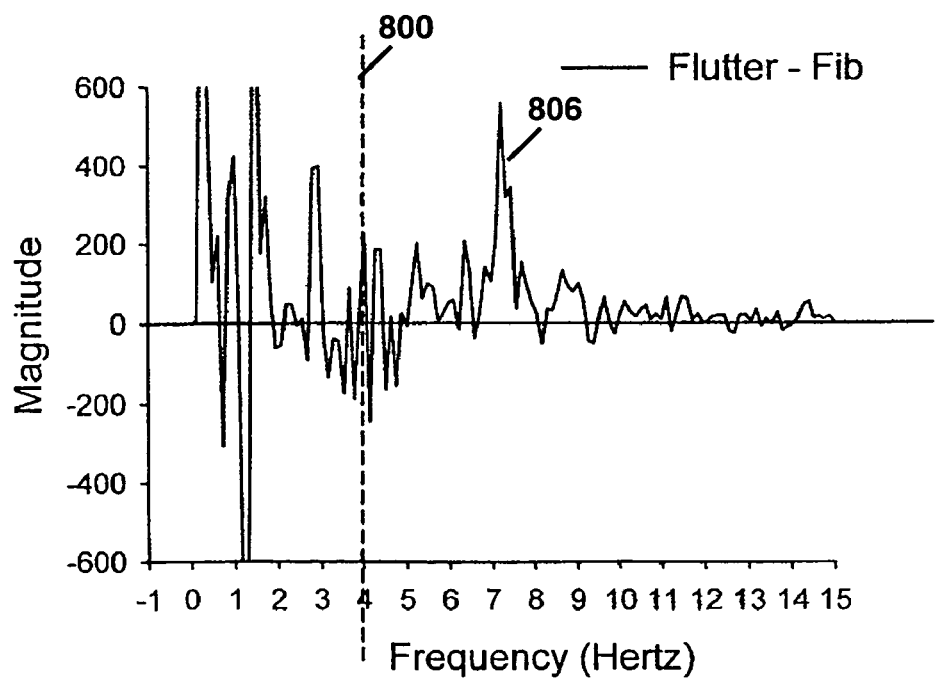
FIG. 10B is a graph of the difference in the magnitude of the Fourier transform of an atrial pressure signal during AFL and ventricular fibrillation.

FIG. 10B is a graph of the difference in the magnitude of the Fourier transform of an atrial pressure signal during AFL and ventricular fibrillation. A prominent peak 804 occurring at a frequency greater than the threshold frequency 800 is observed. Methods of the present invention may therefore be usefully applied for discriminating atrial arrhythmias based on atrial pressure measurements regardless of the ventricular rhythm present.

Figure 11:
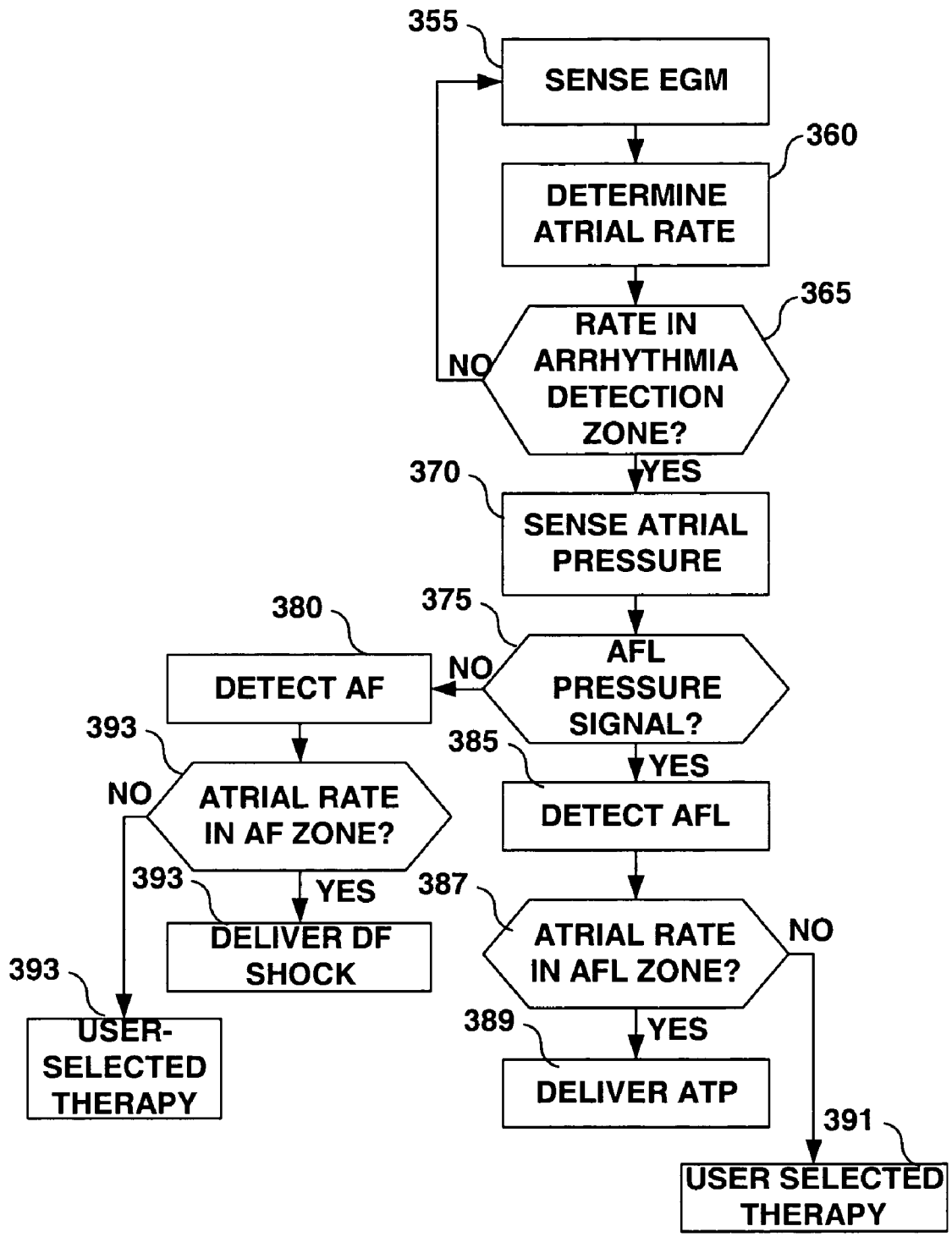
FIG. 11 is a flow chart of a method for selecting an arrhythmia therapy according to an embodiment of the present invention.

As indicated previously, an arrhythmia therapy selection may be based on the AF or AFL classification made according to the methods described herein. FIG. 11 is a flow chart of a method for selecting an arrhythmia therapy according to the present invention. Typically, an arrhythmia therapy selection will be made to initiate an ATP therapy if the atrial rate falls in the AFL detection zone and the atrial pressure analysis results in a classification of AFL. An arrhythmia therapy selection may be made to deliver a defibrillation shock when the atrial rate is in the AF detection zone and the atrial pressure analysis results in an AF classification. However, if the rate and pressure information are conflicting, for example if the atrial rate falls within an AF zone and the atrial pressure signal analysis indicates AFL, or vice versa (i.e., the atrial rate falls in the AFL zone but the atrial pressure signal analysis indicates AF), a selected therapy may be programmable at the user's option.

For example, if the rate is in the AF zone but atrial pressure analysis indicates AFL, an ATP therapy may be selected first as a more conservative approach. Alternatively, a defibrillation shock may be selected immediately in a more aggressive approach. The approach taken, more conservative or more aggressive, may depend on individual patient considerations and physician preferences.

A method allowing such therapy selection options to be taken is shown in FIG. 11 wherein blocks 355 through 385 correspond to identically numbered blocks shown in FIG. 3. After provisionally detecting an atrial arrhythmia based on rate and classifying the arrhythmia as AFL or AF based on atrial pressure at block 385 or block 380, respectively, the method shown in FIG. 11 determines if the rate and pressure information support a common arrhythmia classification.

After classifying the rhythm as AFL at block 385 based on atrial pressure signal analysis performed at block 375 according to any of the methods described above, a determination is made whether the atrial rate falls in the AFL zone at decision block 387. If the rate is in the AFL zone, a programmed menu of therapies for responding to AFL, typically beginning with ATP, is delivered at block 389. However, if the atrial rate is not in the AFL zone, i.e., the rate is in the AF zone, a therapy may be selected at block 391 in accordance with a previously programmed selection made by the physician. The selected therapy under the circumstances of an atrial rate in the AF zone but atrial pressure signal indicating AFL may be ATP or a defibrillation shock or another selected atrial anti-arrhythmia therapy.

Similarly, after classifying the rhythm as AF at block 380 according to an atrial pressure signal analysis at block 375, a determination is made at decision block 393 whether the atrial rate is in the AF zone, in agreement with the AF classification. If so, the AF may be treated customarily with a defibrillation (DF) shock at block 393. If the atrial rate is not in the AF zone, i.e., the rate is in the AFL zone, a therapy may be selected at block 393 according to a previously programmed selection made by the physician. The selected therapy under this circumstance of an atrial rate in the AFL zone but atrial pressure indicating AF may be ATP, defibrillation shock, or other selected therapy depending on physician preferences and individual patient condition.

Some of the techniques described above may be embodied as a computer-readable medium comprising instructions for a programmable processor such as microprocessor 224 or pacing timing and control 212, for example. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

It is apparent from the above description that numerous variations and modifications to the methods described herein may be conceived by one having skill in the art and the benefit of the teachings provided herein without departing from the scope of the present invention. A variety of signal processing techniques may be successfully employed by the methods included in the present invention for determining an indicator of AFL based on an evaluation of the frequency content of an atrial pressure signal in the time or frequency domain. The methods described herein for detecting and classifying an arrhythmia based on rate and pressure may be combined with the use of other arrhythmia detection and/or discrimination variables such as rate variability. Furthermore, and as indicated previously, these methods may be adapted for use in classifying ventricular arrhythmias by employing a ventricular pressure signal for discriminating between ventricular tachycardia and fibrillation. The detailed descriptions of the various embodiments provided herein are therefore intended to be exemplary, rather than limiting, with regard to the following claims.

What is claimed is:

1. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to an atrial signal, the determined cardiac rate corresponds to an atrial rate, and the sensed pressure signal corresponds to an atrial pressure signal, and wherein the first arrhythmia corresponds to atrial flutter and the second arrhythmia corresponds to atrial fibrillation.

2. The method of claim 1, wherein generating the parameter includes processing the sensed pressure signal using time-domain signal analysis.

3. The method of claim 1, wherein generating the parameter includes processing the sensed pressure signal using frequency-domain signal analysis.

4. The method according to claim 1, further comprising selecting a therapy in response to the arrhythmia classification.

5. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to an atrial signal, the determined cardiac rate corresponds to an atrial rate, and the sensed pressure signal corresponds to a ventricular pressure signal, and wherein the first arrhythmia corresponds to atrial flutter and the second arrhythmia corresponds to atrial fibrillation.

6. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to a ventricular signal, the determined cardiac rate corresponds to a ventricular rate, and the sensed pressure signal corresponds to a ventricular pressure signal, and wherein the first arrhythmia corresponds to ventricular tachycardia and the second arrhythmia corresponds to ventricular fibrillation.

7. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein generating the parameter further comprises:
filtering the sensed pressure signal to remove high frequency pressure signals;
subtracting the filtered pressure signal from the sensed pressure signal to generate a high frequency pressure signal; and
determining an amplitude-related parameter in response to the high frequency signal.

8. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein generating the parameter further comprises:
filtering the sensed pressure signal to remove high frequency pressure signals;
subtracting the filtered pressure signal from the sensed pressure signal to generate a high frequency pressure signal;
rectifying the high frequency pressure signal; and
integrating the high frequency pressure signal to determine an integral value.

9. The method according to claim 8, wherein generating the parameter includes comparing the integral value to a tachycardia detection threshold value and classifying the detected arrhythmia as a tachycardia in response to the integral value being greater than the tachycardia detection threshold value and classifying the detected arrhythmia as fibrillation in response to the integral value being less than the tachycardia detection threshold value.

10. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein generating the parameter further comprises:
computing a summation of sampled pressure signal points;
comparing the summation to a previously determined summation of sampled pressure signal points; and
determining a correlation between the summation and the previously determined summation.

11. The method according to claim 10, wherein classifying the arrhythmia includes classifying the arrhythmia as tachycardia in response to the correlation being substantially less than 1 and classifying the arrhythmia as fibrillation in response to the correlation being substantially equal to 1.

12. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein generating a parameter further comprises:
performing a Fourier transform on the sensed pressure signal;
determining the fundamental frequency of the Fourier transform; and
determining if a peak exists at a non-harmonic frequency of the fundamental frequency.

13. The method according to claim 12, wherein classifying the arrhythmia includes classifying the arrhythmia as tachycardia in response to a peak occurring at a non-harmonic frequency of the fundamental frequency, and classifying the arrhythmia as fibrillation in response to a peak not occurring at a non-harmonic frequency of the fundamental frequency.

14. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein generating a parameter further comprises:
performing a Fourier transform on the sensed pressure signal;
defining a threshold frequency separating the low frequency components from the high frequency components of the Fourier transform;
determining a low frequency peak magnitude as the magnitude of a low frequency peak occurring below the threshold frequency;
determining a high frequency peak magnitude as the magnitude of a high frequency peak occurring above the threshold frequency; and
computing a relation between the low frequency peak magnitude and the high frequency peak magnitude.

15. A method for detecting and classifying an arrhythmia, comprising:
sensing a cardiac electrogram signal;
determining a cardiac rate in response to the sensed cardiac electrogram signal;
detecting an arrhythmia in response to the cardiac rate;
sensing an intracardiac pressure signal;
generating a parameter corresponding to a frequency content of the pressure signal;
comparing the parameter to predetermined criteria;
classifying the arrhythmia in response to the comparing, wherein the arrhythmia is classified as a first arrhythmia in response to the parameter meeting the predetermined criteria and as a second arrhythmia in response to the parameter not meeting the predetermined criteria;
selecting a therapy in response to the, wherein selecting a therapy further comprises:
selecting an anti-tachycardia therapy in response to an atrial rate falling within an atrial detection threshold and the arrhythmia being classified as the first arrhythmia;
selecting a defibrillation therapy in response to the atrial rate falling within a fibrillation detection threshold and the arrhythmia being classified as the second arrhythmia;
selecting a first user-defined therapy in response to the atrial rate falling within the atrial detection threshold and the arrhythmia being classified as the second arrhythmia; and
selecting a second user-defined anti-arrhythmia therapy in response to the atrial rate falling within the fibrillation detection threshold and the arrhythmia being classified as the first arrhythmia.

16. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;

means for generating a parameter corresponding to a frequency content of the pressure signal;
means for comparing the parameter to predetermined criteria; and
means for classifying the arrhythmia in response to the comparing,
wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to an atrial signal, the determined cardiac rate corresponds to an atrial rate, and the sensed pressure signal corresponds to an atrial pressure signal, and wherein the first arrhythmia corresponds to atrial flutter and the second arrhythmia corresponds to atrial fibrillation.

17. The device of claim 16, wherein means for generating the parameter includes means for processing the sensed pressure signal using time-domain signal analysis.

18. The device of claim 16, wherein means for generating the parameter includes means for processing the sensed pressure signal using frequency-domain signal analysis.

19. The device according to claim 16, further comprising means for selecting a therapy in response to the arrhythmia classification.

20. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to an atrial signal, the determined cardiac rate corresponds to an atrial rate, and the sensed pressure signal corresponds to a ventricular pressure signal, and wherein the first arrhythmia corresponds to atrial flutter and the second arrhythmia corresponds to atrial fibrillation.

21. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to a ventricular signal, the determined cardiac rate corresponds to a ventricular rate, and the sensed pressure signal corresponds to a ventricular pressure signal, and wherein the first arrhythmia corresponds to ventricular tachycardia and the second arrhythmia corresponds to ventricular fibrillation.

22. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein means for generating the parameter further comprises:
means for filtering the sensed pressure signal to remove high frequency pressure signals;
means for subtracting the filtered pressure signal from the sensed pressure signal to generate a high frequency pressure signal; and
means for determining an amplitude-related parameter in response to the high frequency signal.

23. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein means for generating the parameter further comprises:
means for filtering the sensed pressure signal to remove high frequency pressure signals;
means for subtracting the filtered pressure signal from the sensed pressure signal to generate a high frequency pressure signal;
means for rectifying the high frequency pressure signal; and
means for integrating the high frequency pressure signal to determine an integral value.

24. The device method according to claim 23, wherein means for generating the parameter includes means for comparing the integral value to a tachycardia detection threshold value and classifying the detected arrhythmia as a tachycardia in response to the integral value being greater than the tachycardia detection threshold value and classifying the detected arrhythmia as fibrillation in response to the integral value being less than the tachycardia detection threshold value.

25. A medical device, comprising:
means for sensing a cardiac electrogram signal;

means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein means for generating the parameter further comprises:
means for computing a summation of sampled pressure signal points;
means for comparing the summation to a previously determined summation of sampled pressure signal points; and
means for determining a correlation between the summation and the previously determined summation.

26. The device according to claim 25, wherein means for classifying the arrhythmia includes means for classifying the arrhythmia as tachycardia in response to the correlation being substantially less than 1 and classifying the arrhythmia as fibrillation in response to the correlation being substantially equal to 1.

27. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein means for generating a parameter further comprises:
means for performing a Fourier transform on the sensed pressure signal;
means for determining the fundamental frequency of the Fourier transform; and
means for determining if a peak exists at a non-harmonic frequency of the fundamental frequency.

28. The device according to claim 27, wherein means for classifying the arrhythmia includes means for classifying the arrhythmia as tachycardia in response to a peak occurring at a non-harmonic frequency of the fundamental frequency, and classifying the arrhythmia as fibrillation in response to a peak not occurring at a non-harmonic frequency of the fundamental frequency.

29. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria; and
means for classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein means for generating a parameter further comprises;
means for performing a Fourier transform on the sensed pressure signal;
means for defining a threshold frequency separating the low frequency components from the high frequency components of the Fourier transform;
means for determining a low frequency peak magnitude as the magnitude of a low frequency peak occurring below the threshold frequency;
means for determining a high frequency peak magnitude as the magnitude of a high frequency peak occurring above the threshold frequency; and
means for computing a relation between the low frequency peak magnitude and the high frequency peak magnitude.

30. A medical device, comprising:
means for sensing a cardiac electrogram signal;
means for determining a cardiac rate in response to the sensed cardiac electrogram signal;
means for detecting an arrhythmia in response to the cardiac rate;
means for sensing an intracardiac pressure signal;
means for generating a parameter corresponding to a frequency content of the pressure signal;
means for comparing the parameter to predetermined criteria;
means for classifying the arrhythmia in response to the comparing; and
means for selecting a therapy in response to the arrhythmia classification,
wherein the arrhythmia is classified as a first arrhythmia in response to the parameter meeting the predetermined criteria and as a second arrhythmia in response to the parameter not meeting the predetermined criteria, and wherein means for selecting a therapy further comprises:
means for selecting an anti-tachycardia therapy in response to an atrial rate falling within an atrial detection threshold and the arrhythmia being classified as the first arrhythmia;
means for selecting a defibrillation therapy in response to the atrial rate falling within a fibrillation detection threshold and the arrhythmia being classified as the second arrhythmia;
means for selecting a first user-defined therapy in response to the atrial rate falling within the atrial detection threshold and the arrhythmia being classified as the second arrhythmia; and
means for selecting a second user-defined anti-arrhythmia therapy in response to the atrial rate falling within the fibrillation detection threshold and the arrhythmia being classified as the first arrhythmia.

31. A computer readable medium having computer executable instructions for performing a method comprising:
sensing a cardiac electrogram signal;
determining a cardiac rate in response to the sensed cardiac electrogram signal;

detecting an arrhythmia in response to the cardiac rate;
sensing an intracardiac pressure signal;
generating a parameter corresponding to a frequency content of the pressure signal;
comparing the parameter to predetermined criteria; and
classifying the arrhythmia in response to the comparing, wherein the arrhythmia is classified as a first arrhythmia in response to the parameter meeting the predetermined criteria and as a second arrhythmia in response to the parameter not meeting the predetermined criteria, wherein the sensed cardiac electrogram signal corresponds to an atrial signal, the determined cardiac rate corresponds to an atrial rate, and the sensed pressure signal corresponds to an atrial pressure signal. and wherein the first arrhythmia corresponds to atrial flutter and the second arrhythmia corresponds to atrial fibrillation.

* * * * *